United States Patent [19]
Rogers et al.

[11] Patent Number: 5,736,543
[45] Date of Patent: Apr. 7, 1998

[54] BENZOXAZINES FOR ENHANCING SYNAPTIC RESPONSE

[75] Inventors: Gary A. Rogers, Santa Barbara; Gary S. Lynch, Irvine, both of Calif.

[73] Assignees: The Regents of the University of California, Oakland; Cortex Pharmaceuticals, Inc., Irvine, both of Calif.

[21] Appl. No.: 624,335

[22] Filed: Apr. 3, 1996

[51] Int. Cl.⁶ ............... C07D 265/12; A61K 31/535
[52] U.S. Cl. .................. 514/229.5; 514/214; 544/89; 540/576
[58] Field of Search .................. 544/95; 540/576; 514/214, 229.5

[56] References Cited

U.S. PATENT DOCUMENTS

| | | | |
|---|---|---|---|
| 3,257,396 | 6/1966 | Koo | 544/92 |
| 5,650,409 | 7/1997 | Rogers et al. | 544/89 |

FOREIGN PATENT DOCUMENTS

WO 94/02475  2/1994  WIPO.

OTHER PUBLICATIONS

Takacs et al. "The magnitude of the Stereodirecting Effect on an Allylic Alkoxy-Substituent in an Amidomercuration Cyclization" (1990) *Tetrahedron Letters* 31(47): 6765–6768.

Takacs et al. "A Removable Auxiliary for Amidomercuration Reactions: The Stereoselective Preparation of Substituted N–Acyl Pyrrolidines and Piperidines" (1989) *Tetrahedron Letters* 30(52): 7321–7324.

*Primary Examiner*—John M. Ford
*Attorney, Agent, or Firm*—Townsend and Townsend and Crew LLP

[57] ABSTRACT

Compounds based on the benzoxazine ring system

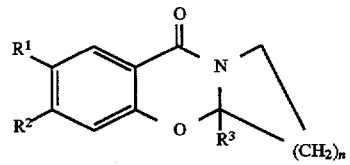

are disclosed for use in enhancing synaptic responses mediated by AMPA receptors. The compounds are effective in the treatment of subjects suffering from impaired nervous or intellectual functioning due to deficiencies in the number or strength of excitatory synapses or in the number of AMPA receptors. The compounds can also be used for the treatment of non-impaired subjects for enhancing performance in sensory-motor and cognitive tasks which depend on brain networks utilizing AMPA receptors, for improving the performance of subjects with memory deficiencies, for treating schizophrenia, and for improving memory encoding.

22 Claims, 1 Drawing Sheet

BENZOXAZINES FOR ENHANCING SYNAPTIC RESPONSE

This invention relates to the prevention and treatment of cerebral insufficiency, including enhancement of receptor functioning in synapses in brain networks responsible for higher order behaviors.

BACKGROUND OF THE INVENTION

The release of glutamate at synapses at many sites in the mammalian forebrain stimulates two classes of postsynaptic receptors. These classes are usually referred to as AMPA/quisqualate and N-methyl-D-aspartic acid (NMDA) receptors. AMPA/quisqualate receptors mediate a voltage-independent fast excitatory post-synaptic current (the "fast epsc") whereas NMDA receptors generate a voltage-dependent, slow excitatory current. Studies carried out in slices of hippocampus or cortex indicate that the AMPA receptor-mediated fast epsc is by far the dominant component at most glutamatergic synapses under most circumstances.

AMPA receptors are not evenly distributed across the brain but instead are largely restricted to the telencephalon and cerebellum. These receptors are found in high concentrations in the superficial layers of neocortex, in each of the major synaptic zones of hippocampus, and in the striatal complex, as reported by Monaghan et al., in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of the AMPA receptor could have significant benefits for intellectual performance. Such drugs should also facilitate memory encoding. Experimental studies, such as those reported by Arai and Lynch, *Brain Research*, 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning. Compounds that enhance the functioning of the AMPA form of glutamate receptors facilitate the induction of LTP and the acquisition of learned tasks as measured by a number of paradigms. Granger et al., *Synapse* 15:326–329 (1993); Staubli et al., *PNAS* 91:777–781 (1994); Arai et al., *Brain Res.* 638:343–346 (1994); Staubli et al., *PNAS* 91:11158–11162 (1994); Shors et al., *Neurosci. Let.* 186:153–156 (1995); and International Patent Application Publication No. WO 94/02475 (PCT/US93/06916) (Lynch and Rogers, Regents of the University of California).

There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992). A possible prototype for a compound that selectively facilitates the AMPA receptor has recently been disclosed by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA receptor-mediated potentials. See, for example, Staubli et al., *Psychobiology* 18:377–381 (1990) and Xiao et al., *Hippocampus* 1:373–380 (1991). Aniracetam has also been found to have an extremely rapid onset and washout, and can be applied repeatedly with no apparent lasting effects; these are valuable traits for behaviorally-relevant drugs. Unfortunately, the peripheral administration of aniracetam is not likely to influence brain receptors. The drug works only at high concentrations (about 1.0 mM), and Guenzi and Zanetti, *J. Chromatogr.* 530:397–406 (1990) report that about 80% of the drug is converted to anisoyl-GABA following peripheral administration in humans. The metabolite, anisoyl-GABA, has been found to have no aniracetam-like effects.

A class of compounds that do not display the low potency and inherent instability characteristic of aniracetam has recently been disclosed. These compounds, termed "ampakines," are disclosed in International Patent Application Publication No. WO 94/02475 (PCT/US93/06916) (Lynch and Rogers, Regents of the University of California). The ampakines are chemically more stable than aniracetam, and show improved bioavailability as judged by experiments performed by Positron Emission Tomography (PET)—see, for example, Staubli et al., in *PNAS* 91:11158–11162 (1994). Additional ampakines in the form of benzoyl piperidines and pyrrolidines have since been discovered and are the subject of pending U.S. patent application Ser. No. 08/458,967, filed Jun. 2, 1995. A new class of ampakines, benzoxazines, have now been discovered to have unexpectedly high activity in in vitro and in vivo models for assessing the probability of producing cognition enhancement. These benzoxazine compounds are the subject of the present invention.

SUMMARY OF THE INVENTION

It has now been discovered that synaptic responses mediated by AMPA receptors are increased by administration of a novel class of benzoxazine compounds, bearing certain similarities to the ampakines but patentably distinct overall. The ability of the novel compounds of this invention to increase AMPA receptor-mediated responses makes the compounds useful in serving a variety of purposes, including facilitating the learning of behaviors dependent upon AMPA receptors, and use as therapeutic drugs in conditions in which AMPA receptors or synapses utilizing these receptors are reduced in numbers or efficiency, or in those circumstances when enhanced excitatory synaptic activity would be beneficial.

These and other aspects and advantages of the invention will become apparent from the description that follows.

BRIEF DESCRIPTION OF THE DRAWING

The figure is a plot of the threshold dose for enhancing memory in test animals vs. the concentration required to increase the width of field excitatory post-synaptic potential at half-height by 50%, comparing three test compounds of the present invention (represented by circles) with structurally analogous compounds of the prior art (represented by diamonds) which lack the fused ring structures of the benzoxazines and are therefore not conformationally restricted (i.e., therefore rotomers).

DETAILED DESCRIPTION OF THE INVENTION AND PREFERRED EMBODIMENTS

Figure 1:
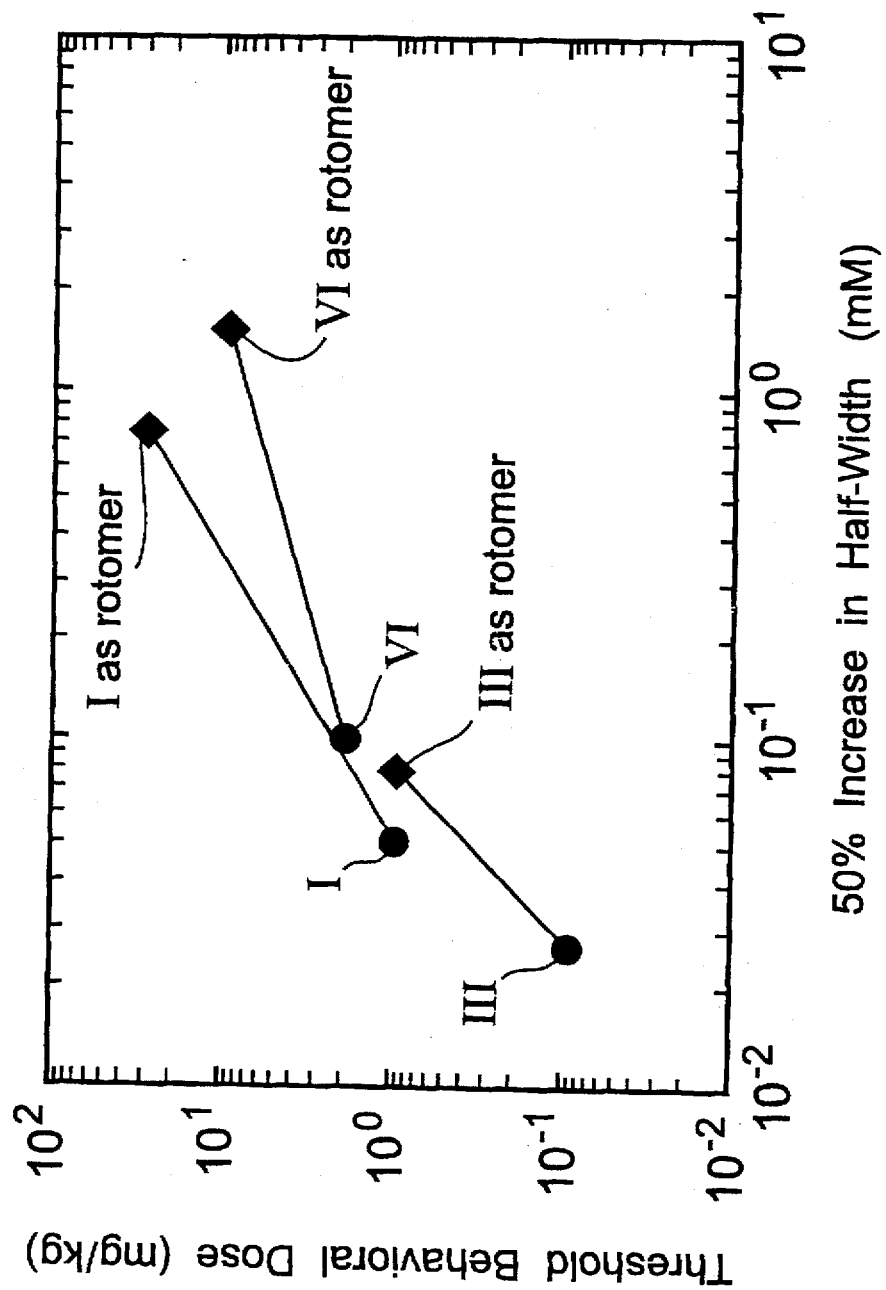

The compounds of the present invention are benzoxazines having the following formula

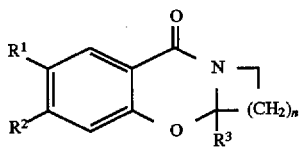

In this formula:

$R^1$ and $R^2$ are either individual monovalent moieties or joined together to form a single divalent moiety. As monovalent moieties, $R^1$ and $R^2$ are either the same or different and are each either H or $R^4O$ provided that at least one of $R^1$ and $R^2$ is $R^4O$, in which $R^4$ is either H, $C_1$–$C_6$ alkyl and halo-substituted $C_1$–$C_6$ alkyl. As a single divalent moiety, $R^1$ and $R^2$ together form either

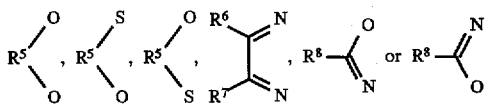

in which:

$R^5$ is either $C(R^9)_2$, $C(R_9)_2C(R^9)_2$ or $CR^9$=$CR^9$, where the $R^9$'s are either H, halogen, $C_1$–$C_6$ alkyl or halo-substituted $C_1$–$C_6$ alkyl and are either the same or different in any $R^5$;

$R^6$ is either H, $C_1$–$C_6$ alkyl or halo-substituted $C_1$–$C_6$ alkyl;

$R^7$ is either H, $C_1$–$C_6$ alkyl or halo-substituted $C_1$–$C_6$ alkyl; and $R^8$ is either H, $C_1$–$C_6$ alkyl or halo-substituted $C_1$–$C_6$ alkyl;

$R^3$ is either H, $C_1$–$C_6$ alkyl or halo-substituted $C_1$–$C_6$ alkyl; and n is 1, 2, 3 or 4.

The term "alkyl" is used herein to include both straight-chain and branched-chain species. Straight-chain species are preferred. $C_1$–$C_3$ alkyls are also preferred, particularly methyl and ethyl, and methyl is the most preferred. The term "halo-substituted" is used herein to include both single and multiple halogen substitutions. Thus, "halo-substituted" alkyl groups include alkyl groups substituted with one, two, three or more halogen atoms, and for those alkyl groups bearing multiple halogen substitutions the term includes alkyl groups bearing two or more different halogen atoms as well as those in which all substitutions are the same halogen. Preferred halogens are chlorine, bromine, and fluorine, with fluorine particularly preferred. Examples of $R^1$ and $R^2$ groups that are halo-subsitituted alkyls are $CH_2FO$, $CHF_2O$, $CF_3O$, $C_2H_5O$, $CH_3$—CHF—O, $CH_3$—$CF_2$—O, $CH_2F$—$CH_2$—O, $CHF_2$—$CH_2$—O, and $CF_3$—$CH_2$—O.

Thus, for those compounds in which $R^1$ and $R^2$ are individual monovalent moieties, preferred compounds are those in which one of these two moieties is H and the other is $R^4O$ where $R^4$ is either $C_1$–$C_6$ alkyl or fluoro-substituted $C_1$–$C_6$ alkyl, with $R^4$ more preferably being either $C_1$–$C_3$ alkyl or fluoro-substituted $C_1$–$C_3$ alkyl, still more preferably $CH_3$ or $CF_3$, and most preferably $CH_3$.

For those compounds in which $R^1$ and $R^2$ are joined together to form a single divalent moiety, preferred compounds are those in which $R^5$ is either $C(R^9)_2$, $C(R^9)_2C(R^9)_2$ or $CR^9$=$CR^9$, in which the $R^9$'s are H, halogen or $C_1$–$C_3$ alkyl; $R^6$ is either H or $C_1$–$C_3$ alkyl; $R^7$ is either H or $C_1$–$C_3$ alkyl; and $R^8$ is either H, $C_1$–$C_3$ alkyl or halo-substituted $C_1$–$C_3$ alkyl. Particularly preferred are those in which $R^5$ is either $CH_2$, $CF_2$, $CH_2CH_2$ or CH=CH; $R^6$ is H; $R^7$ is H; and $R^8$ is H, $CH_3$ or $CF_3$. Most preferred are those in which the divalent moiety is either

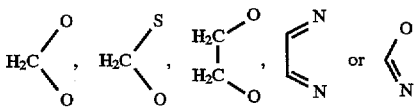

and particularly the first three of these moieties.

Finally, $R^3$ is preferably either H or $C_1$–$C_3$ alkyl, and most preferably either H or $CH_3$, and n is preferably either 2 or 3.

The compounds of the present invention can be synthesized in a variety of ways, using conventional synthetic chemistry techniques. The benzoxazine structure can be synthesized in the following manner. The carboxyl group of an appropriately substituted salicylic acid is activated with carbonyldiimidazole in an anhydrous solvent such as dichloromethane, chloroform, tetrahydrofuran or the like, followed by addition of an aminoalkylacetal, such as $H_2N(CH_2)_3CH(OCH_2CH_3)_2$. The resulting amide is treated with a strong acid, such as an aryl or alkyl sulfonic acid, trifluoroacetic acid or the like, in a solvent of low basicity such as chloroform, dichloromethane or the like, to cleave the acetal and cyclize the intermediate aldehyde with the amide nitrogen and the phenolic oxygen to give rotationally restricted structures of the type shown below:

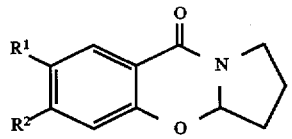

Alternatively, the activated salicylate can be combined with 1-pyrroline or 2,3,4,5-tetrahydropyridine to produce pyrrolobenzoxazines and tetrahydropyridobenzoxazines, respectively.

The salicylic acid derivatives can be synthesized by a variety of methods known to those skilled in the art. One such method is the reaction of an appropriately substituted phenoxide salt with phosgene or carbon dioxide (Kolbe-Schmidt reaction) under conditions that cause rearrangement of the initially formed acyl phenol to the salicylate.

The compounds of this invention can be incorporated into a variety of formulations for therapeutic administration. Examples are capsules, tablets, syrups, suppositories, and various injectable forms. Administration of the compounds can be achieved in various ways, including oral, bucal, rectal, parenteral, and intraperitoneal administration. Dose levels can vary widely, and optimal dosages for any particular patient or condition are readily determinable by those of skill in the art. Typical dosages can range from milligrams to decigrams. Preferred formulations of the compounds are oral preparations, particularly capsules or tablets containing each from about 1 milligram up to about 100 milligrams of active ingredient. Depending on the strength of the compound, a typical dosage may be one 10-mg tablet taken two or three times a day, or one time-release capsule or tablet of 10–100 mg taken once a day. The time-release effect may be obtained by capsule materials that dissolve at different pH values, by capsules that release slowly by osmotic pressure, or by any other known means of controlled release. Subjects contemplated for treatment with the compounds of the invention include humans, domesticated animals, laboratory animals, and livestock.

The compounds of this invention are useful in a variety of ways. They can serve, for example, as research tools for studying the biophysical and biochemical properties of the AMPA receptor and the consequences of selectively enhancing excitatory transmission on the operation of neuronal circuitry. Because the compounds reach central synapses, they will allow for testing of the behavioral effects of enhancing AMPA receptor currents.

As positive modulators or excitatory neuronal communication, the compounds of this invention have many potential applications in humans. For example, increasing the strength of excitatory synapses could compensate for losses of synapses or receptors associated with aging and brain disease (Alzheimer's disease, for example). Enhancing AMPA receptors could cause more rapid processing by multisynaptic circuitries found in higher brain regions and thus could produce an increase in perceptual-motor and intellectual performance. As another example, because increasing AMPA receptor-mediated responses facilitates synaptic changes of the type believed to encode memory, the compounds of this invention are expected to be functional as memory enhancers. Additional applications contemplated for the compounds of this invention include improving the performance of subjects with sensory-motor problems dependent upon brain networks utilizing AMPA receptors, improving the performance of subjects impaired in cognitive tasks dependent upon brain networks utilizing AMPA receptors, improving the performance of subjects with memory deficiencies, treating depression, alcoholism and schizophrenia, and improving the recovery of subjects suffering from trauma.

Accordingly, the compounds of this invention in suitable formulations can be employed for decreasing the amount of time needed to learn a cognitive, motor or perceptual task. Alternatively, these compounds can be employed for increasing the time for which cognitive, motor or perceptual tasks are retained. Still further, these compounds can be employed for decreasing the quantity and/or severity of errors made in recalling a cognitive, motor or perceptual task. Such treatment can prove especially advantageous in individuals who have suffered injury to the nervous system, or who have endured disease of the nervous system, especially injury or disease that affects the number of AMPA receptors in the nervous system.

The following examples are offered for purposes of illustration.

EXAMPLE 1

Preparation of (R,S)-1,3-Dioxolo[4,5-g]-2,3-dihydro-1H-pyrrolo[2,1-b][1,3]benzoxazine-10(3aH)-one (Compound I; per generic formula: $\{R^1+R^2\}$= —O—CH$_2$—O—, $R^3$=H, n=2)

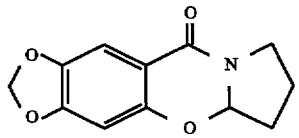

Synthesis was begun with the preparation of 3,4-methylenedioxysalicylic acid from sesamol and phosgene according to the procedure of Sartori et al., *Synthesis* 763–766 (1988). Once prepared, the acid was coupled to 4-aminobutyraldehyde diethyl acetal by the use of carbonyldiimidazole as follows. The carbonyldiimidazole (3.82 g, 23.6 mmol) was dissolved in 50 mL of CH$_2$Cl$_2$, and 3,4-methylenedioxysalicylic acid (4.09 g; 22.5 mmol) was added with stirring. The resulting solution was allowed to stand overnight, followed by the addition of 4-aminobutyraldehyde diethyl acetal (4.45 mL). The solution was then allowed to stand for 24 hours, then refluxed for 15 minutes. Most of the CH$_2$Cl$_2$ was then removed on a rotary evaporator and the residual solution was diluted with diethyl ether and washed with a pH 7.4 phosphate buffer followed by a pH 2 phosphate buffer. The organic solution was dried over Na$_2$SO$_4$ and the solvents were removed on a rotary evaporator to give the amide/acetal in quantitative yield.

The amide/acetal was dissolved in 50 mL of dry CHCl$_3$ to which was added 132 mg camphorsulfonic acid. The resulting solution was allowed to stand overnight, then analyzed by thin-layer chromatography, which indicated complete conversion of starting material to product. UV/Vis (ultraviolet light, visible range) spectra in neutral and basic solutions confirmed that no free phenol remained. Most of the CHCl$_3$ was removed on a rotary evaporator and the resulting yellow oil was covered with 40 mL of diethyl ether, which led to crystallization. The following day the volume of ether was increased to 100 mL, and after one hour the supernatant was decanted into a separatory funnel. The crystals were collected by filtration and washed with diethyl ether and petroleum ether to yield 3.933 g. The ether washes were combined with the mother liquor and washed with 10% Na$_2$CO$_3$ and a saturated solution of NaCl. The solution was dried over Na$_2$SO$_4$ and evaporated to an oil on a rotary evaporator. Addition of diethyl ether afforded an additional 0.513 g for a total yield of 85%. To remove yellow color, the product was passed down a short column of silica gel and eluted with 50% CHCl$_3$/CCl$_4$ followed by 100% CHCl$_3$.

Crystallization was achieved by removal of solvents and addition of diethyl ether to give product with a 98% recovery and melting point of 161.5°–162.2° C. Infrared (IR) spectroscopy (KBr): amide carbonyl at 1655 cm$^{-1}$. $^1$H NMR: δ 7.312 (1H, s); 6.441 (1H, s); 5.983 (2H, s); 5.437 (2H, t, J=5.71 Hz); 3.81 (1H, dt, J=11.47 and 7.12 Hz); 3.58 (1H, ddd, J=11.43, 7.96, and 5.37 Hz); 2.40 (1H, m); 2.22 (1H, m); 2.095 (1H, m); and 1.93 ppm (1H, m) downfield from tetramethylsilane, confirming the structure as that of (R,S)-1,3-dioxolo[4,5-g]-2,3-dihydro-1H-pyrrolo[2,1-b][1,3]benzoxazine-10(3aH)-one. The racemic product was resolved on a Chiralcel OD column and the first eluting enantiomer (hexane/10% isopropanol) was shown to be at least 10-fold more active than the second eluting enantiomer in the in vitro hippocampal slice preparation used to determine the effect on the excitatory post-synaptic potential (EPSP).

EXAMPLE 2

Preparation of (R,S)-1,3-Dioxolo[4,5-g]-1,2,3,4-tetrahydropyrido[2,1-b][1,3]benzoxazine-11(4aH)-one (Compound II; per generic formula: $\{R^1+R^2\}$= —O—CH$_2$—O—, $R^3$=H, n=3)

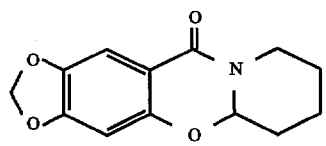

This pyrido analogue of Compound I was prepared in the manner described in Example 1 except that 5-aminopentanal diethyl acetal was used in place of the 4-aminobutyraldehyde diethyl acetal. The synthesis of 5-aminopentanal diethyl acetal from 5-aminopentanol was performed in four steps: (1) protection of the amino group with phthalic anhydride; (2) oxidation of the alcohol by the Swern modification of the Pfitzner/Moffatt reaction; (3) protection of the aldehyde via the diethyl acetal; and (4) removal of the phthaloyl group with ethanolic hydrazine.

These reactions are described in Fieser and Fieser, *Reagents for Organic Synthesis,* Volume 1 (1967), pages 882, 304 and 442, and Volume 2, (1980) page 200 (Wiley Interscience), and are known to those skilled in the art.

Separately, carbonyldiimidazole (1.185 g, 7.31 mmol) was dissolved in $CH_2Cl_2$ (13 mL), and 4,5-methylenedioxysalicylic acid (1.33 g, 1 equivalent) was added with stirring. After 12 hours, the 5-aminopentanal diethyl acetal (1.3 mL) was added and the solution was allowed to stand for three days. The solution was then refluxed for three hours, then diluted with diethyl ether and washed once with water, twice with 0.5N HCl, twice with 5% $NaHCO_3$, and once with a saturated solution of NaCl. The solution was then dried over $Na_2SO_4$ and filtered through $MgSO_4$. The solvent was then removed on a rotary evaporator to yield the acyclic amide/acetal as a yellow oil. The oil was redissolved in $CHCl_3$ (70 mL) and treated with toluenesulfonic acid (100 mg). The solution was stirred at 20° C. for 14 hours, refluxed for 30 minutes, then washed and dried again by the same procedure. The solvent was removed on a rotary evaporator and the resulting yellow solid was purified by silica gel chromatography ($CHCl_3$ elution).

Crystallization from $CHCl_3$/hexane gave white crystals in 90% overall yield with melting point=116.1°–117.4° C. $^1H$ NMR: δ 7.326 (1H, s); 6.396 (1H, s); 5.976 (1H, s); 5.11 (1$H_{ax}$, dd, J=9.83 and 4.17 Hz); 4.41 (1$H_{eq}$, dm, J=13.66 Hz); 2.75 (1$H_{ax}$, td, J=13.16 and 3.49 Hz); 2.16–2.24 (1$H_{eq}$, m); 1.90–1.96 (1$H_{eq}$, m); 1.75–1.85 (2H, m); 1.5–1.6 (1$H_{ax}$, m); and 1.40–1.50 ppm (1$H_{ax}$, qt) confirming the structure as that of (R,S)-1,3-dioxolo[4,5-g]-1,2,3,4-tetrahydropyrido[2,1-b][1,3]benzoxazine-11(4aH)-one.

EXAMPLE 3

Preparation of (R,S)-1,4-Dioxan[2,3-g]-2,3-dihydro-1H-pyrrolo[2,1-b][1,3]benzoxazine-11(3aH)-one
(Compound III; per generic formula: $\{R^1+R^2\}$=—O—$CH_2CH_2$—O—, $R^3$=H, n=2)

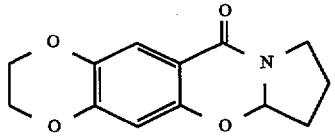

The synthesis of 6-hydroxy-1,4-benzodioxan was performed by first converting 1,4-benzodioxan-6-amine (24.0 g, 0.159 mol) into the bisulfate salt in 200 mL 33% $H_2SO_4$. A chilled suspension of the bisulfate salt was then added to a solution of $NaNO_2$ (14 g; 0.165 mol) in 100 mL of ice water with vigorous stirring. The reaction was allowed to proceed for 20 minutes with addition of ice. The resulting solution of the diazotized amine was slowly poured into 1 L of boiling 10% $H_2SO_4$ over a 15-minute period, then allowed to cool to 20° C. and extracted three times with 100 mL portions of $CH_2Cl_2$. The combined organic layers were washed three times each with 1N HCl, 5% $NaHCO_3$, and saturated NaCl solution. The solution was then dried over $Na_2SO_4$ and the solvent was removed on a rotary evaporator. The resulting viscous oil was dissolved in 250 mL of diethyl ether, allowed to stand overnight, and filtered to remove 1 g of dark solid. The ether was removed on a rotary evaporator and the product phenol was purified by silica gel column chromatography and bulb-to-bulb distillation in a Kugelrohr at a pot temperature of 84°–114° C. The only contaminant observed by $^1H$ NMR was 1,4-benzodioxan. The conversion of 6-hydroxy-1,4-benzodioxan to (R,S)-1,4-dioxan[2,3-g]-2,3-dihydro-1H-pyrrolo[2,1-b][1,3]benzoxazine-11(3aH)-one was performed by a procedure identical to that described in Example 1 above.

The intermediate salicylic acid was characterized by (1) UV spectroscopy: $\lambda_{max}$=317, 251,222 (sh), and 208 nm; (2) IR spectroscopy (KBr): carbonyl at 1660 and 1685 $cm^{-1}$; and 3) $^1H$ NMR: δ 10.142 (1H, s); 7.392 (1H, s); 6.476 (1H, s); and 4.21–4.33 ppm (4H, m). The benzoxazine product was characterized by (1) m.p.=155°–157° C; (2) IR spectroscopy: carbonyl at 1660 $cm^{-1}$; and (3) $^1H$ NMR: δ 7.442 (1H, s); 6.457 (1H, s); 5.426 (1H, t, J=5.8 Hz); 4.21–4.30 (4H, m); 3.806 (1H, dt, J=11.52 and 7.27 Hz); 3.56–3.62 (1H, m); 2.36–2.43 (1H, m); 2.17–2.25 (1H, m); 2.04–2.13 (1H, m); and 1.86–1.96 ppm (1H, m).

Collectively, these data confirmed the structure of the product as that of (R,S)-1,4-dioxan[2,3-g]-2,3-dihydro-1H-pyrrolo[2,1-b][1,3]benzoxazine-11(3aH)-one. The racemic product was resolved on a Chiralpak AD column and the second eluting enantiomer (hexane/50% isopropanol) was shown to be at least 10-fold more active than the first eluting enantiomer in an in vitro hippocampal patch preparation used to determine the effect on AMPA receptor function. This isomer was determined to be the (+)-enantiomer.

EXAMPLE 4

Preparation of (R,S)-6-Methoxy-2,3-dihydro-1H-pyrrolo[2,1-b][1,3]benzoxazine-9(3 aH)-one
(Compound IV; per generic formula: $R^1$=$R^3$=H, $R^2$=$OCH_3$ and n =2)

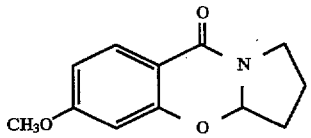

The procedure of Example 1 was followed with 4-methoxysalicylic acid as the starting material. FABMS (fast atom bombardment mass spectrometry): P+1=220 (base peak); $P_2$+1=439. $^1H$ NMR: δ 7.850 (1H, d, J=8.63 Hz); 6.65 (1H, dd, J=8.67 and 2.37 Hz); 6.45 (1H, d, J=2.29 Hz), 5.486 (1H, t, J=5.77 Hz); 3.823 (3H, s) 3.823 (1H, m); 3.6 (1H, m); 2.38–2.46 (1H, m); 2.20–2.28 (1H, m); 2.06–2.15 (1H, m); and 1.89–1.98 ppm (1H, m). Collectively, these analyses confirmed the structure of the product as that of (R,S)-6-methoxy-2,3-dihydro-1H-pyrrolo[2,1-b][1,3]benzoxazine-9(3aH)-one.

EXAMPLE 5

Preparation of (R,S)-7-Methoxy-2,3-dihydro-1H-pyrrolo[2,1-b][1,3]benzoxazine-9(3aH)-one
(Compound V; per generic formula: $R^1$=$OCH_3$, $R^2$=$R^3$=H and n=2)

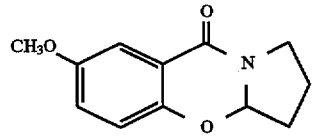

A procedure identical to that described in Example 1 above was followed, except that the starting material was 5-methoxysalicylic acid. EIMS (electron impact mass spectrometry): m/z=219 (P), 150 (base peak, P minus $C_4H_7N$); $^1H$ NMR: δ 7.413 (1H, d, J=3.05 Hz); 7.00 (1H, dd, J=8.82 and 2.96 Hz); 6.894 (1H, d, J=8.84 Hz); 5.456 (1H, t, J=5.82 Hz); 3.826 (3H, s); 3.81–3.88 (1H, m); 3.59–3.65 (1H, m); 2.39–2.46 (1H, m); 2.20–2.28 (1H, m); 2.08–2.16 (1H, m); and 1.89–1.99 ppm (1H, m). Collectively, these analyses confirmed the structure of the product as that of (R,S)-7-methoxy-2,3-dihydro-1H-pyrrolo[2,1-b][1,3]benzoxazine-9(3aH)-one.

EXAMPLE 6

Preparation of (R,S)-Pyrazino[2,3-g]-2,3-dihydro-1H-pyrrolo[2,1-b][1,3]benzoxazine-11(3aH)-one (Compound VI; per generic formula: {R$^1$+R$^2$}=—N=CH—CH=N—, R$^3$=H, and n=2)

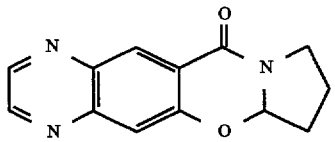

A solution was prepared by dissolving 4-aminosalicylic acid (12.0 g, 78.4 mmol) in 50 mL of formic acid with stirring. A gray solid began to separate after 5 minutes and was collected by filtration after 24 hours. The solid was resuspended in diethyl ether, collected by filtration, and dried under vacuum to yield 14.0 g (99% yield) of the formanilide. UV spectrum: $\lambda_{max}$ (in HCl)=304 and 267 nm. $^1$H NMR: δ 8.85 (0.38H, d, J=10.89 Hz) and 8.35 ppm (0.62H, d, J=1.34 Hz) for the formyl proton in two conformations.

Nitration of the protected aniline was performed in neat trifluoroacetic acid (TFA) using NaNO$_3$. Specifically, N-formyl-4-aminosalicylic acid (15.0 g, 82.9 mmol) was suspended in 450 g of TFA. Sodium nitrate (17.6 g) was added at once to the suspension and at 6 minutes a cooling bath was applied in order to maintain the reaction temperature at 20° C. After 24 minutes an additional 3.5 g of NaNO$_3$ was added and at 29 minutes no starting material was visible. After 30 minutes the reaction was quenched by pouring the TFA solution on approximately 1.8 L of ice and water. The resulting yellow solid was collected by filtration and dried in vacuo for 12 hours to yield 13.70 g (73% yield) of N-formyl-4-amino-5-nitrosalicylic acid. UV/Vis spectra: λ (HCl)=340 and 255 nm; (NaOH) 414 and 286 nm.

The deprotection of the anilino moiety of N-formyl-4-amino-5-nitrosalicylic acid was performed in methanolic HCl by dissolving the product from the preceding paragraph in 125 mL of hot methanol, followed by addition of 10 mL of 12N HCl. A first crop of yellow crystals (6.93 g) was obtained by filtration, and concentration of the mother liquor yielded additional product for a total of 10.45 g (87% yield) of 4-amino-5-nitrosalicylic acid. UV/Vis spectra: λ (HCl)=381 and 317 nm; (NaOH) 400 nm. $^1$H NMR: δ 8.76 (1H, s) and 6.32 ppm (1H, s).

Reduction of the 4-amino-5-nitrosalicylic acid was performed by catalytic hydrogenation over a palladium catalyst. Specifically, 3.37 g (17.0 mmol) of the nitroaromatic compound was dissolved in the minimum volume of tetrahydrofuran (THF), diluted with an equal volume of ethanol, and treated with 2 mL 12N HCl and 150 mg of 10% Pd/C. Hydrogenation was conducted under 58 psi H$_2$ gas for 15.5 hours. A green solid was isolated by filtration and washed with a small volume of THF/ethanol. The solid was suspended in 15 mL water and dissolved by the addition of 4 mL concentrated NH$_4$OH. The solution was filtered to remove the catalyst and then acidified to pH 3 with 12N HCl. The product was collected by filtration and dried to yield 1.7 g of diamine. The mother liquor was chilled in ice water and an additional 0.4 g of product was obtained to give a total of 2.10 g (74% yield). UV spectra: λ (HCl)=301 and 274 nm; (NaOH) 321 and 265 nm. $^1$H NMR: δ 7.72 (1H, s) and 6.28 ppm (1H, s).

The diamine from the preceding paragraph was converted to 7-hydroxy-6-quinoxaline carboxylic acid by reaction with glyoxal. This was accomplished by preparing a solution of 2.0 g (11.9 mmol) of 4,5-diaminosalicylic acid in 20 mL of water containing 5.0 g of Na$_2$CO$_3$ and adding 5.5 g glyoxal bisulfite addition complex (dihydrate form). After standing overnight, the thick mixture was stirred manually, and after a further three hours, the mixture was diluted to a volume of 80 mL with ethanol to yield 450 mg of the sodium salt of the product (after Soxelet extraction with acetone). The original mother liquor was acidified with 2 mL 12N HCl and the resulting chocolate-brown solid was collected by filtration and washed with water to yield (after drying under vacuum) 1.185 g of product (total yield=70%). UV/Vis spectra: λ (H$_2$O) 362 and 303 nm; (6N HCl) 404, 329, and 268 nm; (NaOH) 406, 320 (sh), and 261 nm. $^1$H NMR: δ 8.82 (1H, d, J=1.42 Hz); 8.74 (1H, d, J=1.40 Hz); 8.70 (1H, s); and 7.457 ppm (1H, s).

Activation of the acid for coupling to an amine was performed by conversion to the nitrophenyl ester. Specifically, the acid (2.77 g, 14.6 mmol) was dissolved in 20 mL dry pyridine and treated with 1.0 g 4-nitrophenol and 10 g 4-nitrophenyl trifluoroacetate, added in four portions over ten minutes. Soon after the last addition, the entire mass solidified and was allowed to stand overnight. The mixture was diluted with 20 mL diethyl ether, poured into an additional 200 mL of diethyl ether, and stirred for 10 minutes. After the solid had settled, much of the supernatant was decanted and more diethyl ether was added. The chocolate-brown solid was collected by filtration and crushed to a fine powder under an additional 100 mL of diethyl ether plus 10 mL 100% ethanol for 2 minutes. The solid was collected by filtration and placed under high vacuum until pyridine could no longer be detected (by smell). Final weight=3.28 g of nitrophenyl ester (72% yield). UV spectroscopy confirmed the time-dependent release of nitrophenol in aqueous bicarbonate. $^1$H NMR: δ 10.32 (1H, s, phenol); 8.95 (1H, s); 8.89 (1H, d, J=1.3 Hz); 8.81 (1H, d, J=2.21 Hz); 8.40 (2H, d, J=9.05 Hz); 7.637 (1H, s); and 7.58 ppm (2H, d, J=8.96 Hz).

Treatment of the nitrophenyl ester with 4-aminobutyraldehyde diethyl acetal in dry THF provided the desired acyclic amide/acetal in 97% yield (after purification by silica gel chromatography) with melting point=79.3°–80.3° C. $^1$H NMR: δ 12.424 (1H, s, PhOH); 8.79 (1H, unresolved doublet); 8.69 (1H, d, J=1.34 Hz); 8.236 (1H, s); 7.552 (1H,s); 7.35 (1H, br s, NH); 4.59 (1H, m, acetal methine); 3.70–3.77 (2H, m); 3.53–3.60 (4H, m); 1.79–1.83 (4H, m); and 1.234 ppm (6H, t, J=7.13 Hz).

The acyclic amide/acetal was deprotected and cyclized by the procedure of Example 1 except with TFA as the acid catalyst. Removal of solvent on a rotary evaporator and dilution of the resulting oil with diethyl ether resulted in rapid crystallization to yield 96% of crude product. Purification by silica gel chromatography and crystallization from CHCl$_3$/diethyl ether gave product in final yield of 91% with melting point =185.2°–185.4° C. EIMS: m/z=241 (P); 172 (base, P—C$_4$H$_7$N). IR spectrum: amide at 1673 cm$^{-1}$. $^1$H NMR: δ 8.837 (1H, d, J=1.53 H); 8.814 (1H, d, J=1.53 Hz); 8.766 (1H, s); 7.63 (1H, s); 5.63 (1H, t, J=5.94 Hz); 3.95

(1H, dt, J=11.75 and 7.50 Hz); 3.70–3.76 (1H, m); 2.51–2.58 (1H, m); 2.31–2.39 (1H, m); 2.15–2.24 (1H, m); and 1.97–2.06 ppm (1H, m). Collectively, these analyses confirmed the structure of the product as that of (R,S)-pyrazino[2,3-g]-2,3-dihydro-1H-pyrrolo[2,1-b][1,3]benzoxazine-11(3aH)-one.

EXAMPLE 7

Preparation of (R,S)-Pyrazino[2,3-g]-1,2,3,4-tetrahydropyrido[2,1-b][1,3]benzoxazine-12(4aH)-one (Compound VII; per generic formula: {$R^1$+$R^2$}=—N=CH—CH=N—, $R^3$=H, and n=3)

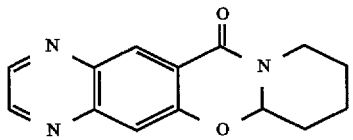

The synthesis of this compound started with the nitrophenyl ester that was generated in Example 6 above. Specifically, the ester (205 mg, 0.66 mmol) was suspended in 5 mL THF and coupled to 150 μL of 5-aminopentanal diethyl acetal (prepared as described in Example 2 above). The amide/acetal was separated from the nitrophenol byproduct by silica gel chromatography and then treated with 6 drops of trifluoroacetic acid in 5 mL of $CHCl_3$. After 24 hours the solution was concentrated and applied to a column of silica gel. Elution with 10% diethyl ether/$CHCl_3$ afforded a nearly white residue that was crystallized from $CHCl_3$/diethyl ether to yield 127 mg (76% yield) of product. EIMS: m/z =255 (P); 172 (base, P—$C_5H_9N$); and 144 (base-CO). $^1$H NMR: δ 8.82 (1H, d, J=1.56 Hz); 8.79 (2H, s and d, J=2.36 Hz); 7.555 (1H, s); 5.376 (1Hax, dd, J=9.95 and 4.07 Hz); 4.64 (1Heq, dm, J=13.74 Hz); 2.88 (1Hax, td, J=13.19 and 3.74 Hz); 2.30–2.38 (1Heq, m); 1.98–2.05 (1Heq, m); 1.85–1.95 (2H, m); and 1.5–1.7 ppm (2H, m), collectively confirming the structure as that of (R,S)-pyrazino[2,3-g]-1,2,3,4-tetrahydropyrido[2,1-b][1,3]benzoxazine-12(4aH)-one.

EXAMPLE 8

Preparation of (R,S)-7-Methoxy-3a-methyl-2,3-dihydro-1H-pyrrolo[2,1-b][1,3]benzoxazine-9-one (Compound VIII; per generic formula: $R^1$=$OCH_3$, $R^2$=H, $R^3$=$CH_3$ and n =2)

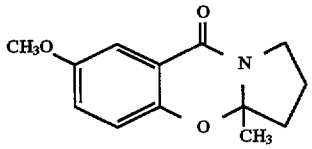

The synthesis of this compound was performed by activating 5-methoxysalicylic acid and combining it with 2-pyrroline. Specifically, 5-methoxysalicylic acid (1.21 g, 7.20 mmol) was suspended in 12 mL $CH_2Cl_2$, and carbonyldiimidazole (1.19 g) was added with stirring. After 3.5 hours, 2-pyrroline (0.71 mL) was added, and the solution was allowed to stand for 5 days. UV spectra in water and $Na_2CO_3$ revealed no free phenol. The solution was then diluted with diethyl ether and washed three times with small volumes of 0.5N HCl, then three times with 5% $NaHCO_3$, and then dried over $Na_2SO_4/K_2CO_3$. After being filtered through $MgSO_4$, the solution was concentrated to an orange oil and purified by silica gel chromatography to yield 0.916 g (55% yield) of product as a yellow oil that solidified upon standing. $^1$H NMR: δ 7.405 (1H, d, J=3.15 Hz); 6.99 (1H, q, J=8.86 and 3.12 Hz); 6.85 (1H, d, J=8.84 Hz); 3.85 (1H, dr, J=11.89 and 8.14 Hz); 3.82 (3H, s); 3.60–3.66 (1H, m); 2.34–2.42 (1H, m); 2.24–2.30 (1H, m); 2.05—2.13 (1H, m); 1.89–1.99 (1H, m); and 1.498 ppm (3H, s). This confirmed the structure as that of (R,S)-7-methoxy-3a-methyl-2,3-dihydro-1H-pyrrolo[2,1-b][1,3]benzoxazine-9-one.

EXAMPLE 9

In Vitro Physiological Testing

The physiological effects of the compounds of this invention were determined in vitro with slices of rat hippocampus by measuring excitatory responses (field EPSPs) in hippocampal slices maintained in a recording chamber continuously perfused with artificial cerebrospinal fluid (ACSF). During a 15–30 minute interval, the perfusion medium was switched to one containing various concentrations of the test compounds. Responses collected immediately before and at the end of drug perfusion were superimposed in order to calculate both the percent increase in EPSP amplitude and percent increase in the width of the response at one-half the peak height (half-width).

To conduct these tests, the hippocampus was removed from anesthetized, 2 month old Sprague-Dawley rats, and in vitro slices (400 micrometers thick) were prepared and maintained in an interface chamber at 35° C. using conventional techniques. this is the procedure used by Dunwiddie and Lynch, J. Physiol. 276:353–367 (1978). The chamber was constantly perfused at 0.5 mL/min with ACSF containing (in mM): NaCl, 124; KCl, 3; $KH_2PO_4$, 1.25; $MgSO_4$, 2.5; $CaCl_2$, 3.4; $NaHCO_3$, 26; glucose, 10; and L-ascorbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activated a population of the Schaffer-commissural (SC) fibers which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field excitatory post-synaptic potential or field "EPSP") which is recorded by a high impedance recording electrode positioned in the middle of the stratum radiatum of CA1.

For the experiments summarized in the table below, the intensity of the stimulation current was adjusted to produce half-maximal EPSPs (typically about 1.5–2.0 mV). Paired stimulation pulses were given every 40 seconds with an interpulse interval of 200 msec. The field EPSPs of the second response were digitized and analyzed to determine amplitude, half-width, and response area. If the responses were stable for 15–30 minutes (baseline), test compounds were added to the perfusion lines for a period of about 15 minutes. The perfusion was then changed back to regular ACSF.

Paired-pulse stimulation was used since stimulation of the SC fibers in part activates interneurons which generate an inhibitory postsynaptic potential (IPSP) in the pyramidal cells of CA1. This feed-forward IPSP typically sets in after the EPSP reaches its peak. The feed-forward IPSP accelerates the repolarization and shortens the decay phase of the EPSP, and thus could partially mask the effects of the test compounds. One of the relevant features of the feed-forward IPSP is that it cannot be reactivated for several hundred milliseconds following a stimulation pulse. This phenomenon can be employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses, as reported by Kessler et al., *Brain Res.* 560:337–341 (1991, and drugs that selectively block the receptor selectively block the field EPSP, as reported by Muller et al., *Science* 242:1694–1697 (1988). Aniracetam increases the mean open time of the AMPA receptor channel and thereby increases the amplitude of the synaptic current and prolongs its duration. Tang et al. *Science* 254:288–290 (1991). These effects are mirrored in the field EPSP, as reported in the literature. See, for example, Staubli et al., *Psychobiology* 18:377–381 (1990); Xiao et al., *Hippocampus* 1:373–380 (1991); and Staubli et al., *Hippocampus* 2:49–58 (1992). Similar results have been reported for the previously disclosed stable benzamide derivatives of aniracetam in International Patent Application Publication No. WO 94/02475 (PCT/US93/06916) (Lynch and Rogers, Regents of the University of California).

The compounds of the invention were assayed in the physiological test system described above for the generation of data presented in the table below. The first data column of the table shows the estimate of the concentration of each test compound that would be required to increase the amplitude of the EPSP to a value 25% above the baseline level. The second data column shows the estimate of the concentration of each test compound that would be required to increase the width of the EPSP at half-height by 50%. Values have been estimated by interpolation in most cases, but by extrapolation from determined values for others. The compounds produced dose-dependent increases both in maximum amplitude and in half-width and were effective at concentrations as low as 20 μM.

The last column of the table describes the threshold dose for enhancing memory in rats that were tested in a learning paradigm that depends on performance in an 8-arm radial maze as described in Staubli et al., *PNAS* 91:11158–11162 (1994). The figure is a scatter plot that correlates this parameter with the in vitro electrophysiological parameter (concentration of compound required to increase the half-width of the field EPSP response by 50% in a hippocampal slice from rat, as described above) that is used as a predictor of in vivo potency. Illustrated is the improvement in drug potency that is realized upon removing the two degrees of rotational freedom that exist in the ampakines that were disclosed in International Patent Application Publication No. WO 94/02475 (PCT/US93/06916). The graph shows a comparison between three conformationally-restricted compounds of the present invention (Compounds I, III and VI as shown in Examples 1, 3, and 6 above, respectively, and represented on the graph by circles) and the corresponding rotomers that are simple substituted benzoyl piperidines and hence not covered by this invention (represented on the graph by diamonds, joined to the corresponding conformationally restricted compounds by lines). Clearly, for all three comparisons, rotational restriction by formation of the benzoxazine structure resulted in marked enhancement of both the in vitro and in vivo properties and validates in vitro electrophysiology as a predictive tool for behavior. The increased potency in the behavioral task (8-arm radial maze) is most notable for Compound III, which is ten times more potent than the corresponding rotomer as well as the other ampakines of Publication WO 94/02475.

The increase in potency presumably derives from the fact that many nonproductive conformations of the rotomers are absent in the conformationally restricted compounds. However, the result that AMPA receptors would respond to lower concentrations of the conformationally restricted compounds and as a result promote improved cognitive performance could not have been predicted from studies of the rotomers. It must be considered equally likely that selecting one particular conformation among many would have abolished all biological activity. It should be noted in this respect that the aromatic-carbonyl dihedral angle in the energy-minimized structures of the rotomers is calculated to be 36° (ab initio) or 45°–50° (semi-empirical AM1), whereas the same angle in the conformationally restricted compounds is calculated to be 18° (AM1).

TABLE

Compounds and Test Data

| Compound | $R^1$ | $R^2$ | $R^3$ | n | +25% Amplitude (mM) | +50% Half-Width (mM) | Behavioral Dose (mg/kg) |
|---|---|---|---|---|---|---|---|
| I | O—CH$_2$—O | | H | 2 | 0.1 | 0.05 | 1 |
| II | O—CH$_2$—O | | H | 3 | 0.3 | 0.2 | |
| III | O—CH$_2$CH$_2$—O | | H | 2 | >0.03 | 0.02 | 0.1 |
| IV | H | CH$_3$O | H | 2 | >1 | 0.4 | |
| V | CH$_3$O | H | H | 2 | 1 | 0.25 | |
| VI | N=CH—CH=N | | H | 2 | 0.1 | 0.1 | 2 |
| VII | N=CH—CH=N | | H | 3 | 0.4 | 0.3 | |
| VIII | CH$_3$O | H | CH$_3$ | 2 | >0.3 | 0.4 | |

The foregoing is offered primarily for purposes of illustration. It will be readily apparent to those skilled in the art that the dosages, methods of administration, and other parameters of the invention described herein may be further modified or substituted in various ways without departing from the spirit and scope of the invention.

We claim:

1. A compound having the formula

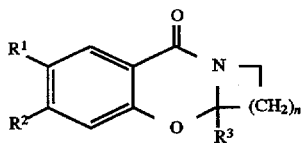

in which:

$R^1$ and $R^2$ together form a single divalent moiety selected from the group consisting of

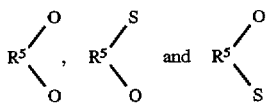

in which:

R⁵ is a member selected from the group consisting of $C(R^9)_2$, $C(R^9)_2C(R^9)_2$ and $CR^9=CR^9$, in which the $R^9$'s are members selected from the group consisting of H, halogen, $C_1$–$C_6$ alkyl and halo-substituted $C_1$–$C_6$ alkyl and are either the same or different in any $R^5$;

$R^3$ is a member selected from the group consisting of H, $C_1$–$C_6$ alkyl and halo-substituted $C_1$–$C_6$ alkyl; and n is 1, 2, 3 or 4.

2. A compound in accordance with claim 1 in which $R^1$ and $R^2$ together form a single divalent moiety selected from the group consisting of

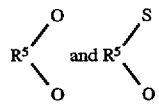

3. A compound in accordance with claim 2 in which:

R⁵ is a member selected from the group consisting of $C(R^9)_2$, $C(R^9)_2C(R^9)_2$ and $CR^9=CR^9$, in which the $R^9$'s are members selected from the group consisting of H, halogen and $C_{1-C3}$ alkyl and are either the same or different in any $R^5$.

4. A compound in accordance with claim 2 in which:

R⁵ is a member selected from the group consisting of $CH_2$, $CH_2CH_2$ and $CH=CH$.

5. A compound in accordance with claim 1 in which $R^3$ is a member selected from the group consisting of H and $C_1$–$C_3$ alkyl.

6. A compound in accordance with claim 1 in which $R^3$ is a member selected from the group consisting of H and $CH_3$.

7. A compound in accordance with claim 1 in which n is 2 or 3.

8. A compound in accordance with claim 1 in which $R^1$ and $R^2$ together form

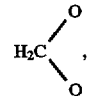

$R^3$ is H, and n is 2.

9. A compound in accordance with claim 1 in which $R^1$ and $R^2$ together form

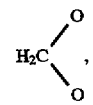

$R^3$ is H, and n is 3.

10. A compound in accordance with claim 1 in which $R^1$ and $R^2$ together form

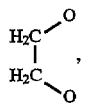

$R^3$ is H, and n is 2.

11. A method for the treatment of a subject to enhance synaptic response mediated by AMPA receptors, said method comprising administering to said subject an effective amount of a compound having the formula

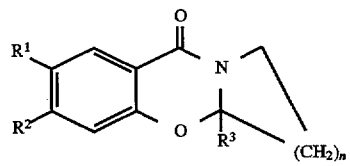

in which:

$R^1$ and $R^2$ together form a single divalent moiety selected from the group consisting of

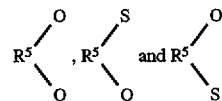

in which:

R⁵ is a member selected from the group consisting of $C(R^9)_2$, $C(R^9)_2C(R^9)_2$ and $CR^9=CR^9$, in which the $R^9$'s are members selected from the group consisting of H, halogen, $C_1$–$C_6$ alkyl and halo-substituted $C_1$–$C_6$ alkyl and are either the same or different in any $R^5$;

$R^3$ is a member selected from the group consisting of H, $C_1$–$C_6$ alkyl and halo-substituted $C_1$–$C_6$ alkyl; and n is 1, 2, 3 or 4.

12. A method in accordance with claim 11 in which $R^1$ and $R^2$ together form a single divalent moiety selected from the group consisting of

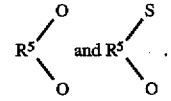

13. A method in accordance with claim 12 in which:

R⁵ is a member selected from the group consisting of $C(R^9)_2$, $C(R^9)_2C(R^9)_2$ and $CR^9=CR^9$, in which the $R^9$'s are members selected form the group consisting of H, halogen and $C_1$–$C_3$ alkyl and are either the same or different in any $R^5$.

14. A method in accordance with claim 12 in which:

R⁵ is a member selected from the group consisting of $CH_2$, $CH_2CH_2$ and $CH=CH$.

15. A method in accordance with claim 11 in which $R^1$ and $R^2$ together form a single divalent moiety selected from the group consisting of

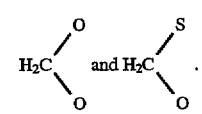

16. A method in accordance with claim 11 in which $R^1$ and $R^2$ together form a single divalent moiety selected from the group consisting of

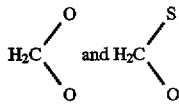

17. A method in accordance with claim 11 in which $R^3$ is a member selected from the group consisting of H and $CH_3$.

18. A method in accordance with claim 11 in which $R^3$ is a member selected from the group consisting of H and $C_1-C_3$ alkyl.

19. A method in accordance with claim 11 in which n is 2 or 3.

20. A method in accordance with claim 11 in which $R^1$ and $R^2$ together form

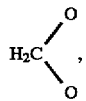

$R^3$ is H, and n is 2.

21. A method in accordance with claim 11 in which $R^1$ and $R^2$ together form

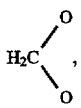

$R^3$ is H, and n is 3.

22. A method in accordance with claim 11 in which $R^1$ and $R^2$ together form

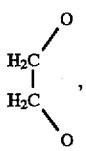

$R^3$ is H, and n is 2.

* * * * *